(12) United States Patent
Mok et al.

(10) Patent No.: US 9,165,045 B2
(45) Date of Patent: Oct. 20, 2015

(54) CLASSIFYING INFORMATION CAPTURED IN DIFFERENT FORMATS FOR SEARCH AND DISPLAY

(71) Applicant: Peoplechart Corporation, San Francisco, CA (US)

(72) Inventors: Megan Mok, Pacifica, CA (US); R. David Holvey, Pacifica, CA (US)

(73) Assignee: PeopleChart Corporation, San Francisco, CA (US)

( * ) Notice: Subject to any disclaimer, the term of this patent is extended or adjusted under 35 U.S.C. 154(b) by 0 days.

(21) Appl. No.: 14/054,316

(22) Filed: Oct. 15, 2013

(65) Prior Publication Data
US 2014/0046931 A1 Feb. 13, 2014

Related U.S. Application Data

(63) Continuation of application No. 13/562,191, filed on Jul. 30, 2012, now Pat. No. 8,572,021, which is a continuation of application No. 12/399,894, filed on Mar. 6, 2009, now Pat. No. 8,250,026.

(51) Int. Cl.
*G06F 17/30* (2006.01)
*G06F 19/00* (2011.01)

(52) U.S. Cl.
CPC .... *G06F 17/30557* (2013.01); *G06F 17/30554* (2013.01); *G06F 19/322* (2013.01); *G06F 19/3443* (2013.01)

(58) Field of Classification Search
None
See application file for complete search history.

(56) References Cited

U.S. PATENT DOCUMENTS

| | | | |
|---|---|---|---|
| 5,664,109 | A | 9/1997 | Johnson et al. |
| 5,729,730 | A | 3/1998 | Wlaschin et al. |
| 6,163,775 | A | 12/2000 | Wlaschin et al. |
| 6,192,165 | B1 | 2/2001 | Irons |
| 6,240,407 | B1 | 5/2001 | Chang et al. |
| 6,263,330 | B1 | 7/2001 | Bessette |
| 6,338,056 | B1 | 1/2002 | Dessloch et al. |
| 6,674,924 | B2 | 1/2004 | Wright et al. |
| 6,886,136 | B1 | 4/2005 | Zlotnick et al. |
| 6,934,698 | B2 | 8/2005 | Judd et al. |
| 6,980,976 | B2 | 12/2005 | Alpha et al. |

(Continued)

OTHER PUBLICATIONS

Pogue, "Windows XP Home Edition: The Missing Manual, 2nd Edition," 2004, pp. 40-41.

(Continued)

*Primary Examiner* — Richard Bowen
(74) *Attorney, Agent, or Firm* — Brian N. Young; Fountainhead Law Group P.C.

(57) ABSTRACT

In one embodiment, a method receives a plurality of documents. The documents may be received from different medical providers. Also, the documents may be medical record documents generated or captured in a first format and a second format. The first format may be an unstructured data format and the second format may be a structured data format. The first and second documents are then converted to a common format. For example, a common format may emerge as the most restrictive or constrained denominator of the first format and the second format. A schema is determined that provides an organizational structure with categories that can be used to index the content of the first and second documents while they are being converted to the common format. The schema and indexing enable the different formats of documents to be combined and organized simultaneously into a single view for a comprehensive review.

16 Claims, 11 Drawing Sheets

(56) References Cited

U.S. PATENT DOCUMENTS

| | | | |
|---|---|---|---|
| 7,016,963 | B1 | 3/2006 | Judd et al. |
| 7,386,462 | B2 | 6/2008 | Silva-Craig et al. |
| 7,627,588 | B1 | 12/2009 | Mohan et al. |
| 7,689,544 | B2 | 3/2010 | Koenig |
| 7,707,169 | B2 | 4/2010 | Comaniciu et al. |
| 7,774,301 | B2 | 8/2010 | Johnson et al. |
| 7,849,049 | B2 | 12/2010 | Langseth et al. |
| 7,895,219 | B2 | 2/2011 | Abrams et al. |
| 7,949,629 | B2 | 5/2011 | Pollara |
| 8,060,376 | B2 | 11/2011 | Horner |
| 8,140,584 | B2 | 3/2012 | Guha |
| 8,250,026 | B2 | 8/2012 | Mok et al. |
| 8,290,951 | B1* | 10/2012 | Joa et al. .................. 707/736 |
| 8,572,021 | B2 | 10/2013 | Mok et al. |
| 8,595,245 | B2* | 11/2013 | Cavestro et al. ............ 707/758 |
| 2002/0004727 | A1 | 1/2002 | Knaus et al. |
| 2002/0035578 | A1 | 3/2002 | Stratigos et al. |
| 2002/0128998 | A1* | 9/2002 | Kil et al. .......................... 707/1 |
| 2002/0138476 | A1 | 9/2002 | Suwa et al. |
| 2002/0152245 | A1 | 10/2002 | McCaskey et al. |
| 2003/0033275 | A1 | 2/2003 | Alpha et al. |
| 2003/0037302 | A1 | 2/2003 | Dzienis |
| 2003/0120458 | A1* | 6/2003 | Rao et al. ..................... 702/181 |
| 2003/0140044 | A1 | 7/2003 | Mok et al. |
| 2004/0044659 | A1 | 3/2004 | Judd et al. |
| 2004/0049478 | A1 | 3/2004 | Jasper et al. |
| 2004/0098664 | A1 | 5/2004 | Adelman et al. |
| 2004/0202386 | A1 | 10/2004 | Quine |
| 2006/0053133 | A1* | 3/2006 | Parkinson .................... 707/101 |
| 2006/0294101 | A1* | 12/2006 | Wnek ............................... 707/7 |
| 2007/0009158 | A1 | 1/2007 | Geva et al. |
| 2007/0011134 | A1 | 1/2007 | Langseth et al. |
| 2007/0011175 | A1 | 1/2007 | Langseth et al. |
| 2007/0033229 | A1* | 2/2007 | Fassett et al. .............. 707/104.1 |
| 2007/0162308 | A1 | 7/2007 | Peters |
| 2007/0168382 | A1 | 7/2007 | Tillberg et al. |
| 2007/0244859 | A1* | 10/2007 | Trippe et al. ..................... 707/3 |
| 2007/0282769 | A1* | 12/2007 | Bierner ........................... 706/20 |
| 2008/0133455 | A1 | 6/2008 | Giordano |
| 2008/0154927 | A1 | 6/2008 | Johnson et al. |
| 2009/0164416 | A1 | 6/2009 | Guha |
| 2009/0228428 | A1* | 9/2009 | Dan et al. ......................... 707/1 |
| 2009/0248619 | A1* | 10/2009 | Das et al. ......................... 707/2 |
| 2009/0259487 | A1 | 10/2009 | Rao et al. |
| 2010/0114899 | A1* | 5/2010 | Guha et al. .................... 707/741 |

OTHER PUBLICATIONS

Gilbert et al. "The New Data Integration Frontier: Unifying Structured and Unstructured Data," ID No. G00138004, 2006 Gartner, Inc. Publication Date; Mach 31, 2006.

U.S. Appl. No. 12/399,894 filed Mar. 6, 2009, titled "Combining Medical Information Captured in Structured and Unstructured Data Formats for Use or Display in a User Application, Interface, or View".

* cited by examiner

```
MSH|^~\&|LIS|DLS|EMR-JoeHumphry|EMR-JoeHumphry|200506221740481-1000||ORU^R01|5|P|2.3|
PID|1|222-22-2222|||Smith2^John H||19560509|M
PV1|1|||16532^HUMPHRY,JOSEPHAL~DLS|||||||||||||||||||||||||||||||
OBR|1|U5455740|5180^CBC w/ Diff^AL~DLS|||200506221440|||||||||6532^HUMPHRY,JOSEPHAL~DLS|||||F|||
OBX|1|ST|5201^White Blood Cell Count^AL~DLS||16.8|x10(9)/L|4.8-10.8|||F|||
OBX|2|ST|5202^Red Blood Cell Count^AL~DLS||4.74|x10(12)/L|4.00-6.20|||F|||
OBX|3|ST|5203^Hemoglobin^AL~DLS||13.8|g/dL|14.0-18.0|L||F|||
OBX|4|ST|5204^Hematocrit^AL~DLS||40.8|fL|42.0-52.0|L||F|||
OBX|5|ST|5205^MCV^AL~DLS||86.1|fL|82.0-101.0|||F|||
OBX|6|ST|5206^MCH^AL~DLS||29.2|pg|26.0-34.0|||F|||
OBX|7|ST|5207^MCHC^AL~DLS||33.9|g/dL|32.0-36.0|||F|||
OBX|8|ST|5280^Neutrophil^AL~DLS||56|%|40-80|||F|||
OBX|9|ST|5282^Band^AL~DLS||NORM|%|0-6|||F|||
OBX|10|ST|5283^Lymphocyte^AL~DLS||31|%|12-44|||F|||
OBX|11|ST|5284^Monocyte^AL~DLS||6|%|0-12|||F|||
OBX|12|ST|5285^Eosinophil^AL~DLS||7|%|0-7|||F|||
OBX|13|ST|5286^Basophil^AL~DLS||0|%|0-2|||F|||
OBX|14|ST|5287^Reactive Lymph^AL~DLS||DNR|%|0-|||F|||
OBX|15|ST|5289^Metamyelocyte^AL~DLS||DNR|%|0-|||F|||
OBX|16|ST|5295^Nucleated RBC^AL~DLS||DNR|/100 WBC|NONE|||F|||
OBX|17|ST|5460^Platelet Count^AL~DLS||285|x10(9)/L|140-440|||F|||
OBX|18|ST|5288^RBC Morphology^AL~DLS||NORM||||F|||
OBX|19|ST|5301^Anisocytosis^AL~DLS||DNR||NONE|||F|||
OBX|20|ST|5302^Microcytosis^AL~DLS||DNR||NONE|||F|||
OBX|21|ST|5304^Hypochromasia^AL~DLS||DNR||NONE|||F|||
OBX|22|ST|5303^Macrocytosis^AL~DLS||DNR||NONE|||F|||
OBX|23|ST|5306^Poikilocytosis^AL~DLS||DNR||NONE|||F|||
OBX|24|ST|5310^Schistocytosis^AL~DLS||DNR||NONE|||F|||
OBX|25|ST|5317^Other WBC / RBC Morphology^AL~DLS||DNR||||F|||
OBX|26|ST|5318^Comments^AL~DLS||DNR||||F|||
OBX|27|ST|5318^Comments^AL~DLS||DNR||||F|||
OBX|28|ST|5220^ABs Neutrophils^AL~DLS||13.1|x|<4.5|||F|||
OBX|29|ST|4601^ARDW^AL~DLS||13.79|x10(9)/L|1.80-7.70|||F|||
PID|2|222-24-2222|||Smith22^Joan B||19440603|F
PV1|2|||16532^HUMPHRY,JOSEPHAL~DLS|||||||||||||||||||||||||||||||
OBR|1|U5461B|5180^CBC w/ Diff^AL~DLS|||200506221050|||||||||6532^HUMPHRY,JOSEPHAL~DLS|||||F|||
OBX|1|ST|5201^White Blood Cell Count^AL~DLS||9.7|x10(9)/L|4.8-10.8|||F|||
OBX|2|ST|5202^Red Blood Cell Count^AL~DLS||4.39|x10(12)/L|3.60-5.40|||F|||
OBX|3|ST|5203^Hemoglobin^AL~DLS||13.7|g/dL|12.0-16.0|||F|||
OBX|4|ST|5204^Hematocrit^AL~DLS||41.3|fL|37.0-47.0|||F|||
OBX|5|ST|5205^MCV^AL~DLS||94.0|fL|82.0-101.0|||F|||
OBX|6|ST|5206^MCH^AL~DLS||31.3|pg|26.0-34.0|||F|||
OBX|7|ST|5207^MCHC^AL~DLS||33.2|g/dL|32.0-36.0|||F|||
OBX|8|ST|5280^Neutrophil^AL~DLS||59|%|40-80|||F|||
OBX|9|ST|5282^Band^AL~DLS||NORM|%|0-6|||F|||
OBX|10|ST|5283^Lymphocyte^AL~DLS||33|%|12-44|||F|||
OBX|11|ST|5284^Monocyte^AL~DLS||6|%|0-12|||F|||
OBX|12|ST|5285^Eosinophil^AL~DLS||1|%|0-7|||F|||
OBX|13|ST|5286^Basophil^AL~DLS||1|%|0-2|||F|||
OBX|14|ST|5287^Reactive Lymph^AL~DLS||DNR|%|0-|||F|||
OBX|15|ST|5289^Metamyelocyte^AL~DLS||DNR|%|0-|||F|||
OBX|16|ST|5295^Nucleated RBC^AL~DLS||DNR|/100 WBC|NONE|||F|||
OBX|17|ST|5460^Platelet Count^AL~DLS||354|x10(9)/L|140-440|||F|||
OBX|18|ST|5288^RBC Morphology^AL~DLS||NORM||||F|||
OBX|19|ST|5301^Anisocytosis^AL~DLS||DNR||NONE|||F|||
OBX|20|ST|5302^Microcytosis^AL~DLS||DNR||NONE|||F|||
OBX|21|ST|5303^Macrocytosis^AL~DLS||DNR||NONE|||F|||
OBX|22|ST|5304^Hypochromasia^AL~DLS||DNR||NONE|||F|||
OBX|23|ST|5306^Poikilocytosis^AL~DLS||DNR||NONE|||F|||
OBX|24|ST|5310^Schistocytosis^AL~DLS||DNR||NONE|||F|||
OBX|25|ST|5317^Other WBC / RBC Morphology^AL~DLS||DNR||||F|||
OBX|26|ST|5317^Other WBC / RBC Morphology^AL~DLS||DNR||||F|||
OBX|27|ST|5318^Comments^AL~DLS||DNR||||F|||
```

Fig. 3

| | logged in as: | | Session expires: 1/1/1800 Log Out |
|---|---|---|---|
| PEOPLECAHRT administrator | Manage Document Categories | | |

Home ▶ System ▶ Manage Document Categories | back site map

You must log in to Member site and click the 'Reload Lookup Cache' link on the home page for changes to take affect.
⌐ 400

Insert new Document Category: [____] Add
402 ⌐ 401

| Name | Group | Report Group | |
|---|---|---|---|
| Advance Health Care Directive | Medical | Advanced Health Care Directive | Edit |
| Case Management Notes | Medical | Case Management Services | Edit |
| Duplicate Pages | Medical | Duplicate Pages | Edit |
| Hospital & Surgery: Admitting History & Physical | Medical | Hospital & Surgery | Edit |
| Hospital & Surgery: Cancer Surgical Procedures | Medical | Hospital & Surgery | Edit |
| Hospital & Surgery: Consultations | Medical | Hospital & Surgery | Edit |
| Hospital & Surgery: Discharge Summary | Medical | Hospital & Surgery | Edit |
| Hospital & Surgery: Emergency Room Reports | Medical | Hospital & Surgery | Edit |
| Hospital & Surgery: Nurses' Notes | Medical | Hospital & Surgery | Edit |
| Hospital & Surgery: Operative Procedures | Medical | Hospital & Surgery | Edit |
| Hospital & Surgery: Other Notes | Medical | Hospital & Surgery | Edit |
| Hospital & Surgery: Progress Notes | Medical | Hospital & Surgery | Edit |
| Imaging Tests: Angiogram | Medical | Radiology or Imaging | Edit |
| Imaging Tests: Bone Density Scans | Medical | Radiology or Imaging | Edit |
| Imaging Tests: CAT or CT Scans | Medical | Radiology or Imaging | Edit |
| Imaging Tests: Mammograms | Medical | Radiology or Imaging | Edit |
| Imaging Tests: MRI Scans | Medical | Radiology or Imaging | Edit |
| Imaging Tests: Nuclear Medicine Scan | Medical | Radiology or Imaging | Edit |
| Imaging Tests: Other | Medical | Radiology or Imaging | Edit |
| Imaging Tests: PET Scans | Medical | Radiology or Imaging | Edit |
| Imaging Tests: Reports | Medical | Radiology or Imaging | Edit |
| Imaging Tests: Ultrasounds | Medical | Radiology or Imaging | Edit |
| Imaging Tests: X-Rays | Medical | Radiology or Imaging | Edit |
| Immunizations | Medical | Immunizations | Edit |
| Lab Tests: CBC and Chemistry | Medical | Lab and Cultures | Edit |
| Lab Tests: Electronic Report | Medical | Lab and Cultures | Edit |
| Lab Tests: Hemoglobin | Medical | Lab and Cultures | Edit |
| Lab Tests: HIV Tests | Medical | Lab and Cultures | Edit |
| Lab Tests: Lipid Profile | Medical | Lab and Cultures | Edit |

PEOPLECHART

Mary Jane Adams

Report Generation

Create Report

Title: [ ]

Create Complete Records Report
Create Last 12 Months Report
Create Personal Health Profile Report Saved filters: [ ▼ ]

hide advanced filter

Document Name: [ ]

Date range: [any] [ ] << start end >> [any]

Source: [All ▼]

All: Check Uncheck

Report Group:
- ☑ Medications and Allergies
- ☐ Mental Health
- ☐ Other
- ☑ Physician Notes Author: [All ▼]

Specialization: All: Check Uncheck
- ☑ Allergy & Immunology
- ☑ Anesthesiology
- ☑ Audiology
- ☑ Behavioral Health run filter Format:
- ☑ Include Clinical Documents
- ☑ Include Personal Health Inputs
- ☑ Include Personal Documents
- ☑ Include Messages
- ☑ Include Electronic Labs
- ☑ Include Electronic Medications Save this filter as: [New Filter]  save ☐ Medications and Allergies
- ☑ Allergies
- ☑ Medications
- ☒ Your October 2008 Amoxicillin refill is ready

*Fig. 7*

Patient Test Panel Set

Patient

Name: Jane Doe
Gender: Female
Date of Birth: 12/20/1948     Age: 60
ID: 532

Test Panel Summary

Number of Test Panels: 15
Earliest Observation Date: 3/8/2006
Latest Observation Date: 3/8/2006
Test Counts: Total=47    High=4    Low=4

Ordering Physician: Dr David Ono MD
Laboratory: Clinical Laboratories of Hawaii, LLP Observation Date: 3/8/2006 8:07:00 AM
Original Report Date: 3/11/2006 7:54:28 AM

| # | Test | Result | Flags | Units | Reference Range | Status |
|---|---|---|---|---|---|---|
| 1 | Sodium | 139 | | mmol/L | (133-145) | FINAL |
| 2 | Potassium | 4.2 | | mmol/L | (3.3-5.1) | FINAL |
| 3 | Chloride | 108 | | mmol/L | (96-108) | FINAL |
| 4 | CO2 | 20 | L | mmol/L | (21-31) | FINAL |
| 5 | Anion Gap | 11 | | | (4-16) | FINAL |
| 6 | BUN | 40 | H | mg/dl | (6-19) | FINAL |
| 8 | Glucose | 107 | H | mg/dl | (70-100) | FINAL |
| 9 | Calcium | 8.9 | | mg/dl | (8.4-10.2) | FINAL |
| 10 | GFR (Non-African Amer) | 17 | L | mL/min/1.7 (>59) | | FINAL |
| 11 | GFR (African American) | 21 | L | 3mL2min/1.7 (>59) | | FINAL |
| | Average GFR for 60-69 yr: 85 | | | 3m2 | | |
| | Chronic kidney disease: <60 | | | | | |
| | Kidney failure: <15 | | | | | |
| | Accuracy of the GFR depends on a stable creatinine and may be overestimated in | | | | | |
| | malnutrition, cachexia, and cirrhosis due to reduced muscle mass. | | | | | |
| | Refer to www.nkdep.nih.gov | | | | | |
| 12 | Comments | DNR | | | | FINAL |

*Fig. 8B*

CLASSIFYING INFORMATION CAPTURED IN DIFFERENT FORMATS FOR SEARCH AND DISPLAY

CROSS REFERENCE TO RELATED APPLICATIONS

The present disclosure is a continuation of U.S. patent application Ser. No. 13/562,191, entitled "Classifying Information Captured in Different Formats for Search and Display in an Image-Based Format," filed Jul. 30, 2012, issued as U.S. Pat. No. 8,572,021 on Oct. 29, 2013, which is a continuation of U.S. patent application Ser. No. 12/399,894, entitled "Combining Medical Information Captured in Structured and Unstructured Data Formats for Use or Display in a User Application, Interface, or View," filed Mar. 6, 2009, issued as U.S. Pat. No. 8,250,026 on Aug. 21, 2012, both of which are incorporated by reference in their entirety for all purposes.

BACKGROUND

Particular embodiments generally relate to a document management system.

In document management, information is likely sourced from different data providers that create and store information in their own formats, such as in paper or electronically in a computer system. In the medical field, patient information is migrating toward an increasing use of electronic systems that can store and organize information within a structured database framework as defined by data tables, fields, and values. Mapping or describing information into named fields and defining the relationship of these fields with each other inside a database structure enables the computer system to identify specific data, recognize the difference between one data field from another, and perform analytical tasks such as queries, calculations, and algorithmic functions. A flexible data structure also allows for compilation of information to be organized in different topics and presented in different reports. Structure can be very simple to very complex.

In the medical field, a majority of physicians still create and keep patient information on paper, such as doctor's notes, faxed lab reports, and hand-written prescriptions. To convert paper to an electronic format, the paper document is scanned into an electronic image. In its raw and original state, the difference in content captured by one electronic image cannot be read and is not recognizable by a computer system as being distinctly different from the content of another electronic image. Without the help of descriptive definitions, electronic images are not distinguishable by the computer and are therefore limited in analytical usefulness. For example, a computer cannot differentiate the results of a lab report image from those of another lab report image or from the content of a prescription image for that matter.

These two formats, paper images and machine-readable information stored in a database are usually not compiled together in a manner that would enable a system to search through both formats simultaneously. Rather, a system may store these different formats in separate directories or file folders and may display the information in separate views or in separate web pages of a web-based system. When patient information is presented in paper images or in machine-readable format, but cannot be compiled together in a way that can be organized for searching, sorting, and analysis simultaneously, the usefulness of patient's information is restricted. The result of having disparate information stored in a system that does not allow for simultaneous query and organization presents a missed opportunity in health care for leveraging an available set of more complete information as basis for making decisions and in some cases, may lead to clinical oversights and medical errors.

SUMMARY

Particular embodiments generally relate to the process of combining and organizing information that was originally created in disparate formats. One type of data is created and saved in paper format and includes examples from handwritten notes, text typed on paper, a body of an email message, and word-processing documents.

The content of a paper document is converted to an electronic image. The conversion may use scanning technology or other recognition technology. In its original state, the content of an electronic image cannot be recognized or understood by the computer as being any different from another electronic image. The image data is considered unstructured data.

Another type of data format is a stream of data transmitted in electronic format, where the data values are identified and separated by delimiters and recognized by the computer system as those pertaining to specific data fields (machine-readable data). This format can also pertain to data values already defined and stored in a database.

A third type is self-entered forms that capture data typed or manually selected from a pull-down list of data choices by the user. This latter format is similar to the machine-readable format in that the data fields are already defined in the database. Both of these data formats may be considered structured data.

In one embodiment, a plurality of documents are received from different data providers, such as from healthcare providers, where the medical documents can be captured in paper, electronically transmitted in parsed, delimited format such as data stream from a diagnostic center to a hospital, or self-entered data such as the physician or patient typing information into a computer system. Other examples include audio recordings, video clips, the body of an email message, and word-processing documents.

For the purpose of illustrating the difference between structured and unstructured data, specifically paper-derived, particular embodiments focus between scanned images (from the paper documents) and machine-readable data that is identified or delimited into recognizable database fields. It will be acknowledged that structured and unstructured data may be represented in other forms. These two very different formats are then converted to a common format.

The different types of data formats are converted to a common format, which is then stored in the database with appropriate indices. The image data is tagged (indexed) with various descriptors selected from categories that are the equivalent of data fields, where eventually, these categories can be further rolled up or mapped into broadly defined or higher-level categories such as by topics or sections of a report. The electronically transmitted data, which is already pre-defined by data fields, can be compiled and presented into a rendered report similar to that of a paper document. Together, paper and electronically-transmitted data co-exist in a common format that is identified by similar data labels and fields, and is recognizable and distinguishable by a computer system. Having a common format enables the simultaneous searching of different data formats and the presentation of searched results in a single, organized view. The search is performed with the use of images. For example, a user may choose to search by one or more search categories and the images created from either paper documents or structured data may be returned as results. Moreover, the resulting images from either paper or structured formats may now be displayed together in the same organization schema, folder, or webpage view.

In one embodiment, a common format is defined as the most constraining format between the two formats. In one example, this may be an image format, which is an unstructured format. Thus, the second documents in structured format are converted to unstructured (image) data format.

A schema is a method for organizing a plurality of data categories and super-categories along which unstructured data (document images) and structured data (electronically delimited data) can be classified. The schema includes a list of categories presented in an organized sequence or in order of importance. It provides a directory or a way to organize or group various data classifications that can range from very narrow to broad, for example, by the details of data fields to broadly defined topics, report sections, or report types. The schema enables presentation of both paper images and electronically transmitted data in a single view that is easy to understand, searchable, and selectable or re-classifiable (into a folder or report).

Data classification may be included in the content of both types of data formats, such as author name, creation date, medical organization that provided the document, patient name about whom information is created, diagnosis, or medical specialization for which the content references. These indices or text descriptors offer a way to classify the content on the paper image document and at the same time are applicable to the data fields associated with the electronically transmitted data. Further separation or roll-up of categories for describing or tagging the specific content found in both type of document formats are determined or predetermined by the classification that make sense or that are commonly found in both types of document formats. These sub-categories are then grouped and rolled up to an organizing schema or principle for organizing documents. An image document may be tagged with one or more indices if the paper image contains content that is determined to match one or more categories.

A further understanding of the nature and the advantages of particular embodiments disclosed herein may be realized by reference of the remaining portions of the specification and the attached drawings.

BRIEF DESCRIPTION OF THE DRAWINGS

FIG. 3 depicts an example of structured data delimited by vertical lines that represent the separation of different data fields.

FIG. 4 depicts a table that specifies sub-categories for report groups according to one embodiment.

FIG. 6 shows an interface that can be used to index images according to one embodiment.

FIG. 7 shows an interface that can be used to search for medical records according to one embodiment.

FIG. 8B shows an example of an image-based report generated using structured data according to one embodiment.

DETAILED DESCRIPTION OF EMBODIMENTS

Figure 1:
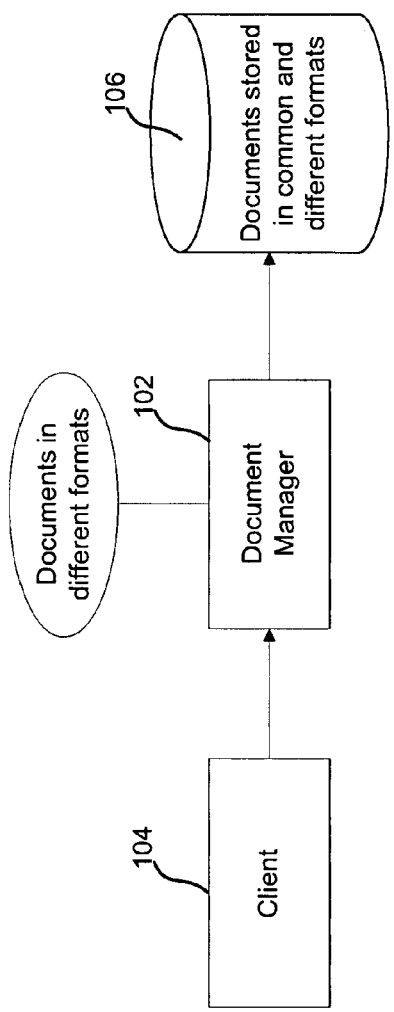
FIG. 1 depicts a simplified system for consolidating and organizing documents according to one embodiment.

FIG. 1 depicts a simplified system 100 for consolidating and organizing documents according to one embodiment. System 100 includes a document manager 102, one or more clients 104, and a database 106. It will be understood that certain elements of system 100 have not been shown, such as networks, other computing devices, etc.

Document manager 102 is configured to receive documents created in different formats. For example, medical records may be received from different medical providers. In one example, a personal health record (PHR) may be managed by a patient. For example, a patient may receive medical care from multiple medical providers who in turn create documents about the episode or portion of care that they had delivered or provided the patient. However, with a PHR system, a patient may consolidate the records in different formats received from a multitude of healthcare providers inside of one system, where the system enables the medical information to be searched, queried, reported, and viewed from a web-based system or from one place. The PHR model provides for comprehensive and portable medical records that are directed by the patient.

Client 104 may include a computing device that is used by a user. The user may want to access different documents in their personal health record. For example, a user may query for documents for a different disease. These documents may have been generated by different medical providers and thus may have been created in different formats. Particular embodiments allow the user to display and search for documents that originated in different formats in a more integrated way inside a single computer system or across a multitude of systems.

The documents may be received in different formats because different medical providers generate the documents in different ways or media. For example, different medical providers may use different systems that create and generate documents in different formats. For example, depending on the type of care and standard of documentation, different documents may be generated in different formats, including physician's notes in paper-based format, x-rays in digital format, medication history transmitted in delimited format, or messages dictated onto word processing documents. Other formats may be contemplated.

A first format is an unstructured data format. Unstructured data is information that cannot be organized into a structure of database tables with descriptive columns and rows of records. For example, in the case of a scanned image of a paper document, the information is not annotated (tagged). In other words, the information is not identifiable or discernible to a computer system. For example, unstructured data may be image-based data, such as a bit map object. Also, textural objects may be unstructured data, such as word processing documents, e-mails, etc. The characteristic of unstructured data is that content displayed on the document cannot easily be read and analyzed by a machine. For example, in its original state, the content of an image of unstructured data cannot be recognized or understood by the computer as being any different from content of another image.

Structured data is in a form where the information can be easily manipulated to generate different reports and can be easily searched. Structured data has an enforced composition to the different types of data in the data structure and this allows for querying and reporting against the data types. The structured data can be manipulated easily to generate different types of documents. In contrast, unstructured data, such as an image, is stored as an image. In its raw form, the information captured by the image, such as the doctor's name, handwritten or typed notes on the document, is not stored or identified as data fields of a database. Thus, the image is not searchable (i.e., a search for documents with the doctor's name would not yield the correct image of the document if the image is not identified in the database).

Particular embodiments take the documents stored in different formats and determine a common format in which to store the documents. For example, a format that is most constraining the formats being used in terms of the ability to name, sort, and parse data by variables may be determined. For example, if the most constraining format is the image format, then both types of documents may be converted to the image format. However, if the most constraining format is structured data, then documents may be stored in the structured data format.

In one embodiment, the common format is an image-based format, which is in unstructured state. Particular embodiments may refer to documents in the common format as electronic images for discussion purposes. However, it will be understood that other formats may be used as the common format even though images is used for discussion purposes.

Data received that is in a structured data format may be converted to an unstructured state. For example, an electronic image of a report may be generated from the structured data. This may be counterintuitive in that most users desire that data is stored in the structured way because of the flexibility and power in manipulating the structured data. However, particular embodiments want to allow a user to search and sort documents that may have originated in different formats. By converting to a common format, the users can simultaneously search, sort, and view documents that may have originated in the different formats even if some advantages of using structured data is lost.

To account for some of the advantages lost by storing structured data in the common format, a schema is used to organize and index document images. By storing the documents in the image-based format and indexing the images using a common schema, the user can search for documents that were originally presented in varied formats. Although two formats, unstructured and structured, are discussed, it will be recognized that different degrees may be contemplated. For example, some documents may have aspects of both unstructured and structured, such as an electronic form that includes data fields and images.

Conventionally, structured data in the form of data fields and unstructured data in the form of scanned images (of paper documents) may have been separately stored in a state where it is not convenient or possible for a user to search through both formats at the same time. Rather, a single search of the structured data may have been performed and then a separate search of the unstructured data may have been performed. Also, when a user wanted to display documents, the documents for structured data and unstructured data were usually not displayed together in a single view, rather in different tabs or in different web pages. However, particular embodiments do allow for the consolidation and display of documents that were originally created in different formats. The schema is used to organize images of both structured and unstructured data in common categories, such that they can be searched and displayed together.

Figure 2:
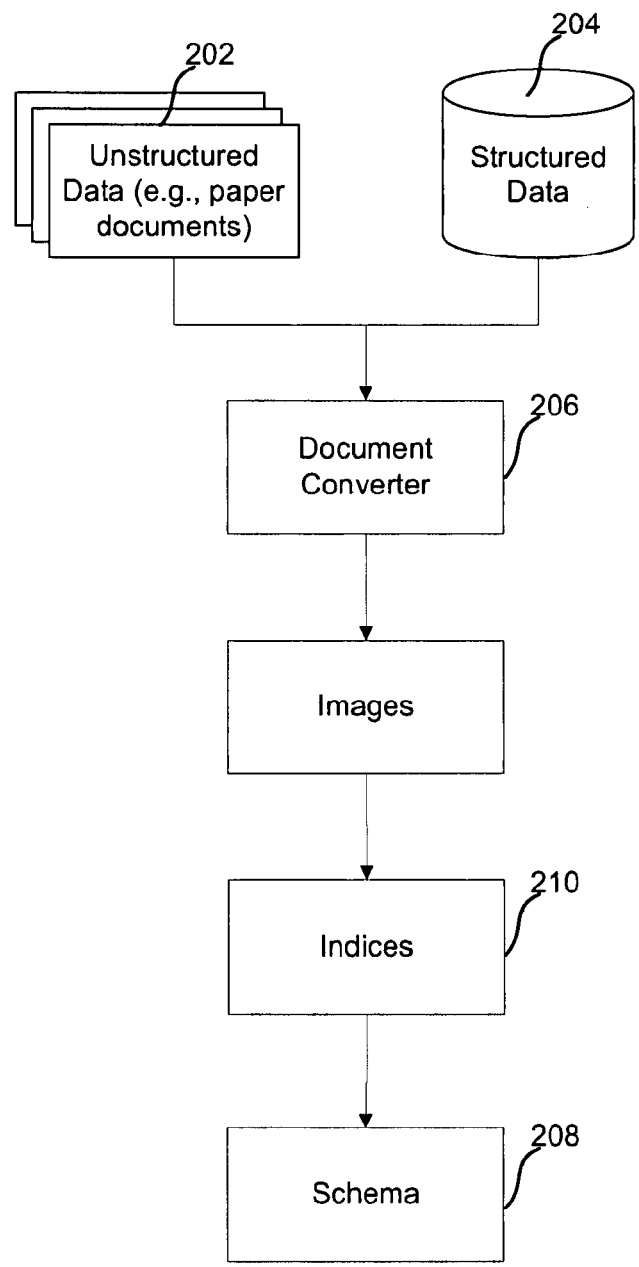
FIG. 2 depicts an example of converting unstructured data and structured data into a common format according to one embodiment.

FIG. 2 depicts an example of converting unstructured data (image documents) and structured data into a common format according to one embodiment. As shown, unstructured data 202 and structured data 204 are being processed by a document converter 206. Document converter 206 is configured to convert unstructured documents 202 and structured data 204 into a common format and organized into a common schema.

In one embodiment, structured data 204 may be received as a stream of text data with each field and its respective value separated by a delimiter or vertical pipeline, as depicted in FIG. 3. The streamed data may be organized by multiple different fields with each field values eventually mapped into a data structure.

Unstructured documents 202 may be any type of unstructured data that is received. For example, images of paper documents may be received or paper documents may be received and scanned into images. In this case, document converter 206 converts unstructured documents 202 into images. If unstructured documents 202 are already in image format, then a conversion is not performed. To convert structured data 204 to images, structured data 204 may be retrieved from different fields of the database. An image report is generated from an aggregation of multiple data values retrieved from the database. The report shows an image of data values on a page. As an image in its basic form, its content is no longer recognizable by a computer.

To provide for some structure to the common format, a schema 208 is used to organize and categorize the image data. The schema is an organizational schema or framework that includes categories from which the images may be organized. Schema 208 may be determined based on expected content that may be included in the images. For example, medical records may have specific information that is included in them, such as a doctor's name, address, diagnosis, prescription, or other categories may usually be found in medical documents and these categories are included in schema 208. Accordingly, an effective organizational schema may be determined in which to classify the images.

Schema 208 is applied to indexing or tagging the document by the various categories. For example, some categories include an author's name, author date, type of page (page categories), and any sub-categories that may be determined. One example of indexing is for a category that includes a doctor's name or ID, any image that includes that doctor's name or ID is indexed with that category. For example, an image identifier may be tagged with that category for the doctor's name or ID. The schema is applied to all images and indices 210 are then generated. The indices may be stored with the images in database 106.

After indexing, structured and unstructured data co-exist in a common format that is identified by similar data labels and fields, and is recognizable and distinguishable by a computer system. This allows searching of images for both document formats simultaneously. For example, a user may search for one of the categories and images created from either unstructured or structured data may be returned. Also, images for both formats of documents may now be displayed simultaneously in the same organization schema, folder, or webpage (view).

In one embodiment, the schema may organize the data in report groups, which are higher level categories. Inside the report groups are section headers that are sub-categories. FIG. 4 discloses an interface that specifies report groups according to one embodiment. A table 400 specifies report groups 401 that have been created for the schema. The report groups 401 may be categories where groups of documents received by a patient can be categorized. For example, in a database, the report group Advanced Health Care Directive is shown as one of the report group categories. A code can be used to identify each report group found in the schema similar to a node on a tree diagram. The code may also be used to determine how to display the report groups. For example, a lower code may cause a report group to be displayed before a higher coded report group.

According to one embodiment, there are specifies sub-categories within each report groups. A column 402 shows the name of various sub-categories that are mapped into a report group 401. The sub-categories are determined based on various data that may be received in each report group. For example, different medical providers may provide different documents to a patient (i.e., in a different format). The documents from different medical providers, however, may be categorized into one of the sub-categories. Any of the report groups (401) and sub-categories (402) can be indices 210.

Schema 208 is then used to index images. Using indices 210, unstructured data may be given some structure to allow for searching and displaying of images. Although structured data 204 was already in a format that could be searched and displayed, to integrate unstructured documents 202 and structured data 204, structured data 204 is converted to the image-based format, which is a more constraining format. That is, an image inherently does not have any structured data to it. However, a common schema 208 is applied to index the images from unstructured documents 202 and structured data 204 to allow integrated searching of both.

Figure 5:
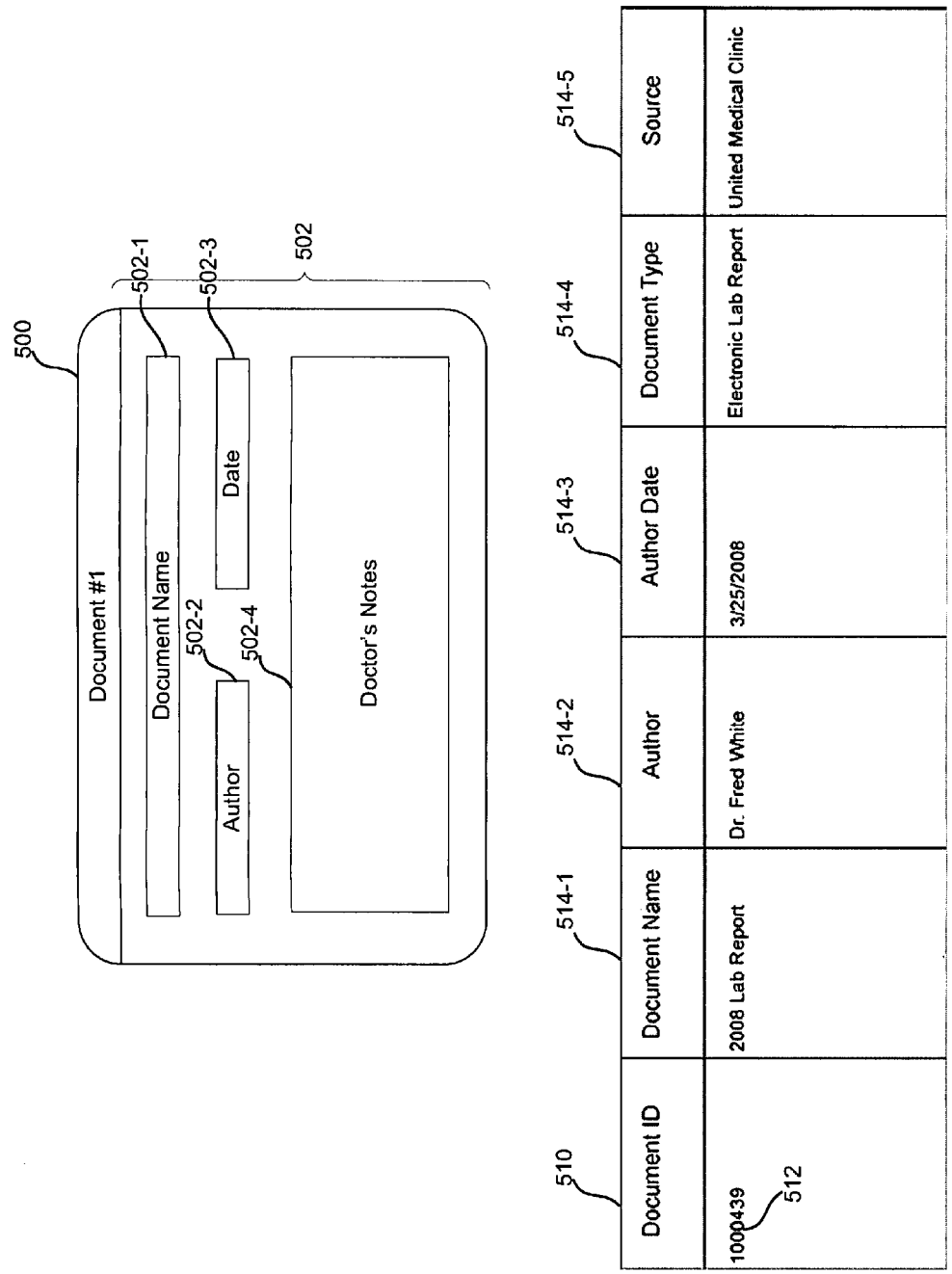
FIG. 5 shows an example of the use of indices for tagging or identifying image data that can be stored as data categories in the database according to one embodiment.

Indices 210 may be stored in a database as field names. FIG. 5 shows an example of a database table that can be used to store indices 210 according to one embodiment. As shown, an image 500 includes content 502. Content 502-1-502-4 may be a document name, Author, Date and Doctor's notes.

This content may be tagged with indices. For example, the document ID may be stored as a row in a table 510. An identifier 512 may be stored to identify image 500. Indices 514 are provided in the columns of table 510. Table 510 may be populated with content from the image or may be organized by category descriptors. For image 500, the fields of the table are filled with data based on the content of the image. For example, for index 514-1, an image's name is inserted into the corresponding data field. Also, the Document name, Author, Author Date, Document Type, and Source may be inserted into the other corresponding fields for indices 514-1 to 514-5.

Table 510 may also include category descriptors that are used to organize the image. For example, the image may fall into different categories based on the content of the image, where the image originated, what medical condition the image is diagnosing, etc. Table 510 may insert information for categories for image 500, such as the document may be associated with the doctor's notes category and the image is tagged in that category. Other categories may or may not be tagged depending on image 500.

Figure 6:
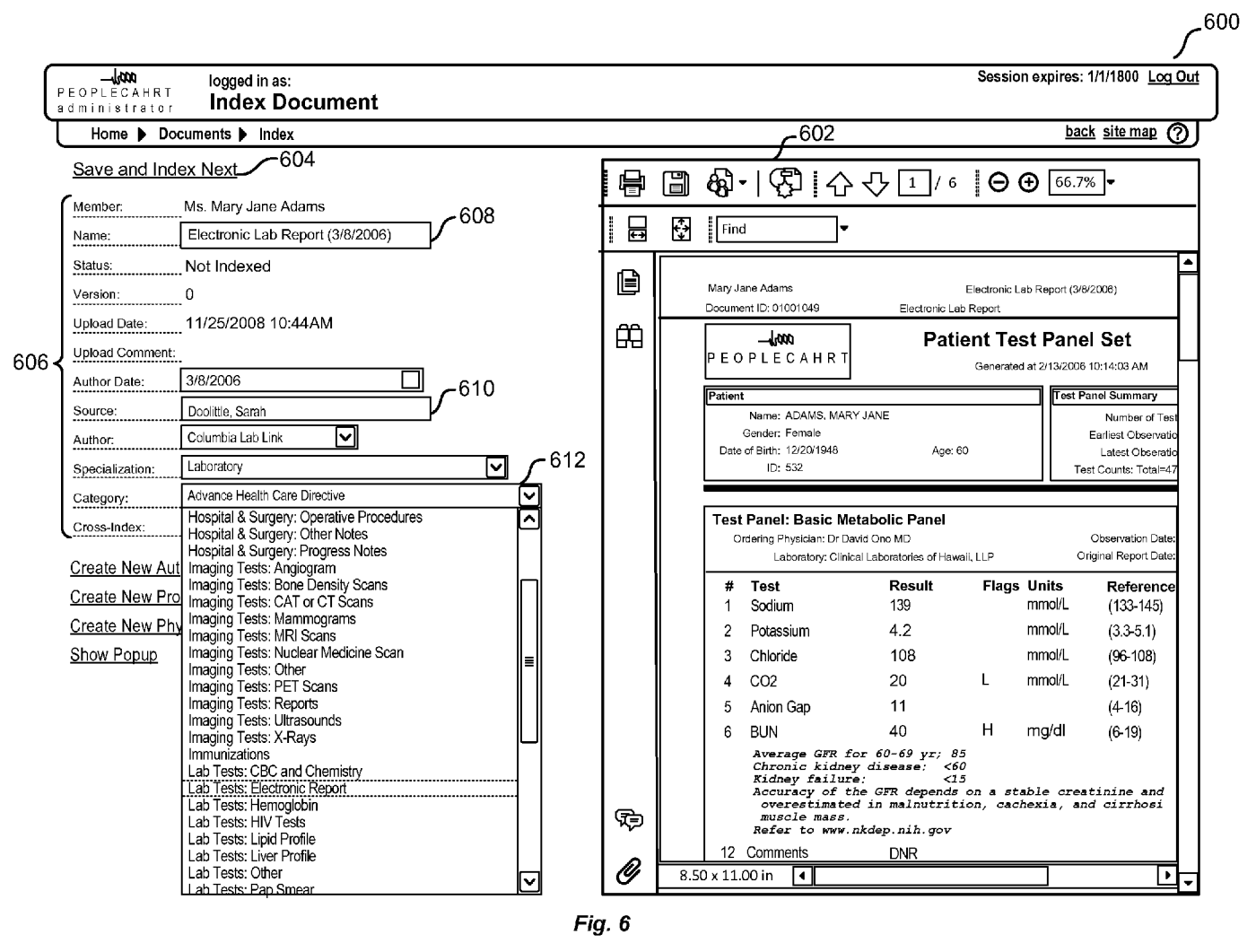

FIG. 6 shows an interface 600 that can be used to index images according to one embodiment. An image 602 is shown that is being indexed. An index section 604 is used to commit and apply attributes or descriptions of the image document 602 in the form of indices. For example, entry boxes 606 are used to receive information that can be used to index image 602. For example, a name 608 and source 610 is used to identify the doctor by name and also the source of where image 602 is received from.

A category 612 is used to categorize image 602. The categories may be used to index image 602 based on the report groups and sub-categories that were described with respect to FIGS. 4A and 4B. When the information is input in index section 604, image 602 is indexed.

Image 602 may be indexed manually or automatically. For example, index section 604 may be used to provide a template for automatically indexing other images. For example, once an image is indexed using interface 600, then other images can be automatically indexed using the template. In one example, similar documents, such as images from the same doctor may be automatically indexed.

After indexing, the images may be searched and displayed. FIG. 7 shows an interface 700 that can be used to search for medical records according to one embodiment. As shown, different categories 702 may be used to search for documents. The categories immunizations, medications and allergies, behavioral health, cardiac electrophysiology, cardiac electroscopy, and cardiology have been selected. For this search, all images that have been indexed with these categories may be retrieved from database 106. By using interface 700, searches may be performed over images that originated from unstructured documents 202 and structured data 204. Separate searches do not need to be performed for the two types of documents.

The schema may be organized by different report groups. For example, different categories of the schema are included in a report group. That is, for a report group Medication and Allergies, the data may be further tagged by specific medical specialties reflecting different diseases categories 704, such as Allergy and Immunology, Anesthesiology, Audiology, Behavioral Health, etc. Any documents tagged with these sub-categories may be searched for and retrieved if the report group hospitalization is used. The organizational schema thus provides some structure with how the images are organized.

Figure 8A:
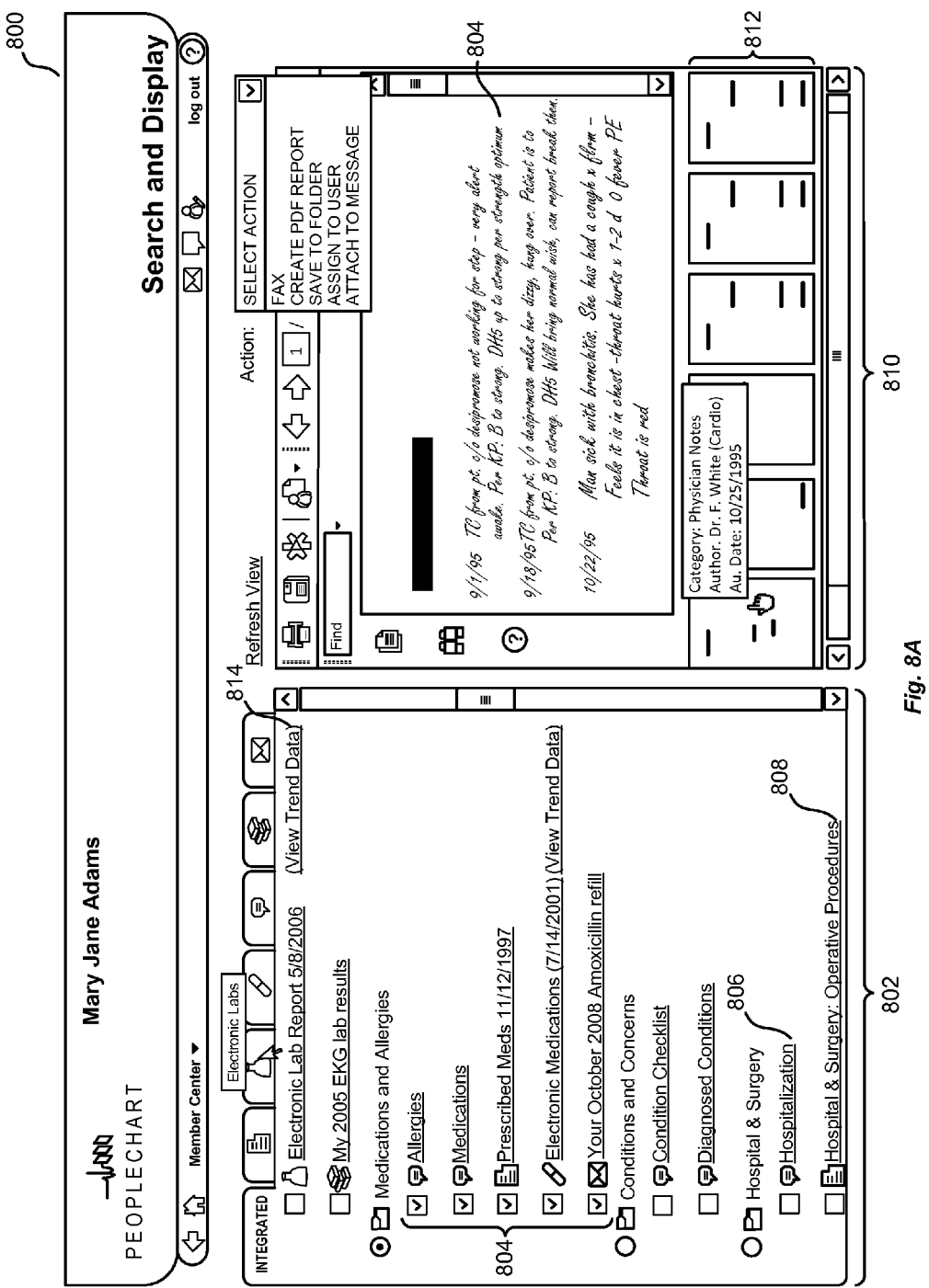
FIG. 8A depicts an example of an interface of search results from reviewing different formats of data provided by different sources according to one embodiment.

FIG. 8A depicts an example of an interface 800 including search results according to one embodiment. As shown in panel 802, links to different images are provided. The images may be images that were generated from documents of different formats. For example, physician notes 804 may be images of paper-based notes. Also, an image 806 may be an image of structured data relating to a record of a hospitalization. Also, an image 808 is an image of notes for the hospitalization. Thus, a user can see different images for different documents under the same report group. For example, all physician notes are categorized together and all images for hospital and surgery are categorized together. Conventionally, electronic hospitalization notes would have been displayed in a different category than paper-based hospitalization notes. By converting the documents to a common format and then indexing them, such as indexing the images with the category "Hospitalization" a search for hospitalization brings up images for documents that originated in different formats.

A preview panel 810 shows images of documents. For example, physician notes 804 are shown, which are mostly composed of handwritten notes and paper-based images. A user may select the different physician notes and have them be displayed. Although not shown, images of documents that originated in different formats may also be included. For example, in preview panel 812 or 804, a document originally populated by structured data as its content is displayed as an image report along side an image of another document that originally was created on paper. In the medication and allergies report group, there are different types of documents as depicted by different icons as shown in 804.

Figure 8C:
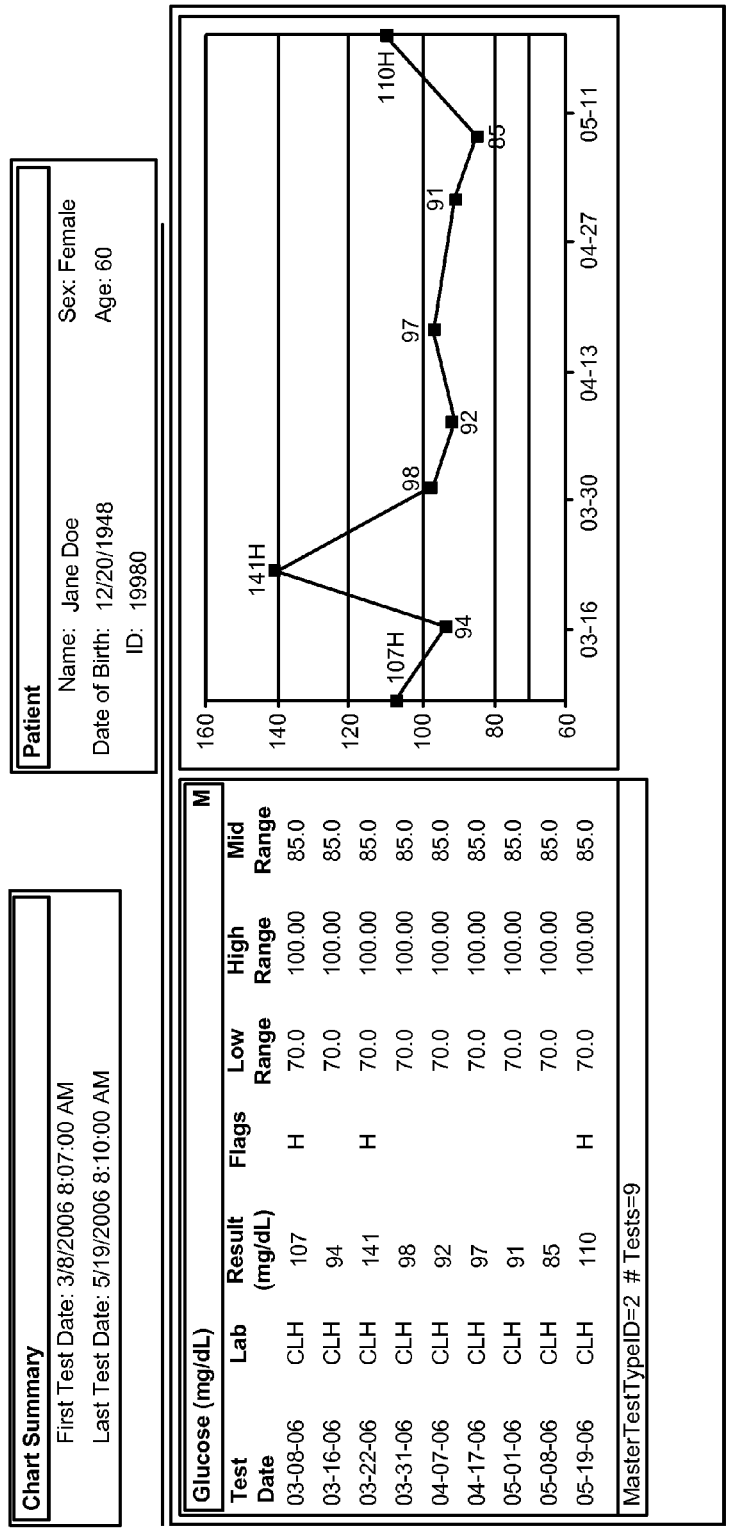
FIG. 8C shows an example of a view of the structured data displayed across time on a graph or chart according to one embodiment.

Interface 800 can be used to view structured and unstructured data and access the benefits of structured data stored in its defined way for greater data manipulation. For example, a link 814 (e.g., the link to View Trend Data) is included in interface 800 to allow a user to access the structured data behind the image. Once link 814 is selected, structured data is retrieved and can be displayed in a timeline or graphical way. For example, a report image may be rendered or generated from the structured data that corresponds to one of the images. FIG. 8B shows an example of an image of a report generated using structured data according to one embodiment. As shown, a test panel is shown. This image is unstructured data in that content found in the image cannot be distinguished by a computer system. However, the schema was used to index the image and it has been retrieved in response to the query received from interface 700 of FIG. 7. When link 814 is selected, a view of the structured data is displayed across time on a graph or chart in FIG. 8C as compared with the rendered snapshot of the data provided by the report image. In this case, structured data that is associated with the image of FIG. 8B is retrieved. The structured data is then used to generate a report as shown. The report may be different from the image if different analytics are desired. However, the report may show the same information as the image; however, it is not in an image format. This may allow further manipulation of the report, such as keyword searching, editing, etc.

Figure 9:
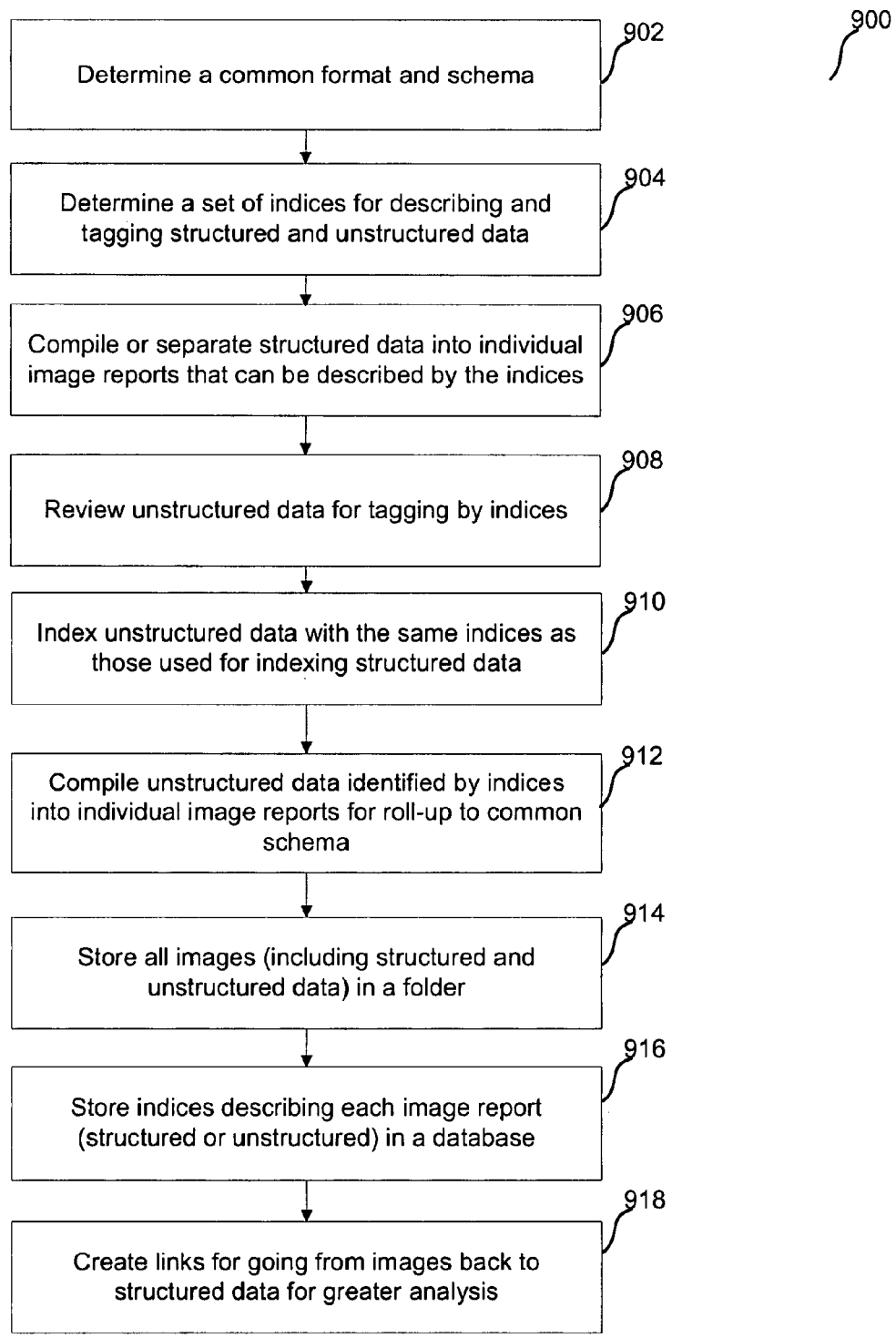
FIG. 9 depicts a simplified flowchart of a method for indexing documents according to one embodiment.

FIG. 9 depicts a simplified flowchart of a method for indexing different data formats according to one embodiment. Step 902 determines a common format. Depending on the format of the unstructured data to be indexed (for example, paper image documents), a different medium or common format may be selected that would be more appropriate for tagging and organizing the content. In one example, a common format is derived from reviewing the most constrained of formats. In one embodiment, the different formats of structured and unstructured data are reviewed and where the most constraining format is selected to become the common format for both types of data. For example, if the only documents to be indexed are structured data, then the common format may be the structured data format. However, if images are to be indexed, then the most constraining common-denominator format is the image-based format. In one embodiment, the formats of documents may be analyzed and the common format is determined automatically.

Step 904 determines the indices to be used for tagging the structured and unstructured-based images. Indices are chosen after reviewing the organizing principle to which a common set of descriptors can be identified to tag and organize the images such that they can all be searched and sorted together. For example, the structured data is tagged by indices and roll-up to image reports along which an organizing schema emerges that can apply to both structured and unstructured-based images. The structured data is parsed into images that are most relevant to the categories of the organizing schema. For example, if a doctor's name is included in the structured data and used to create the image, the image may be indexed with a tag for the doctor's name.

Step 906 compiles or separates structured data into individual image reports that can be described by the indices. The way that structured data is parsed and compiled into individual images is determined by both the nature of the content and the roll-up categories of the common schema from which to apply the organization across all resulting images. For example, the content is analyzed and a report that is considered to represent the data in the most useful manner is determined based on different factors, such as user preferences, conversion rules, etc. Also, the content of the image may be determined based on different categories that could be applied.

Step 908 reviews unstructured data for tagging and indexing. Step 910 uses the schema 208 to index the unstructured data with the same indices as those for images generated from the structured data. The challenge is to apply the right tags or indices for describing the content of an image that is not recognizable or identifiable by a computer system. Particular embodiments provide certain techniques that may be used to index the images. For example, optical character recognition may be performed on the image to determine information from the content of the image. Also, an operator or user may review the image and enter the information. Other methods of extracting information from the unstructured data may be performed. When the information is extracted, it may be matched with categories in schema 208. For example, if a doctor's name is recognized in an image, the image may be tagged with the doctor's name as an index.

Step 912 compiles unstructured data identified by indices into individual image reports for roll-up to common schema (e.g., into report groups as described).

Step 914 stores images of unstructured data and structured data in a file folder. Each image is uniquely described by various data tags or values from a set of indices. The images for the structured data and unstructured data may be stored in the same folder. In step 916, the indices used to identify, describe, or tag each of the images are stored in a database.

Step 918 applies web links for the ability to view the original format of the data of either structured or unstructured data. For example, the links allow for the traversing from the images back to the robustness of structured data. A user can pull up an image and if the user decides to access the structured data that was used to create the image, a link may be used to retrieve the structured data.

Accordingly, views of data in different formats may be generated, organized, and identified in a database through the use of indices. A common schema is applied for further roll-up or classification of the documents after the documents have been converted to a common format. Also, by using a common schema, the documents may be organized in a way that allows for searching and sorting of images created from documents of different formats. This also allows documents from different formats to be displayed on a webpage in an integrated way. Although the technique may convert different formats of data to the most constraining of format as the common format, which may cause structured data to be converted into image data, a user can now search through all documents identified in a category simultaneously instead of searching through different formats of documents separately. Thus, if a user wants to see all documents referencing a hospitalization, any paper-based documents, electronic documents, self-entered documents, or any other documents created can be searched and displayed.

Although the description has been described with respect to particular embodiments thereof, these particular embodiments are merely illustrative, and not restrictive. Although medical records are discussed, other documents may be used.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps treated as sequential in this specification can be performed at the same time.

Particular embodiments may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular embodiments.

Particular embodiments may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of particular embodiments can be achieved by any means as is known in the art. Distributed, networked systems, components, and/or circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A method comprising:
receiving, by a computing device, a plurality of medical documents, the plurality of medical documents including a first set of medical documents in a first format in an image based format and a second set of medical documents in a second format in a structured data format;
determining, by the computing device, a schema based on a review of an organizing principle to which a common set of data fields can be used to classify information from the first set of medical documents and the second set of medical documents;
determining, by the computing device, via extraction, unstructured information in the first set of medical documents relevant to the common set of data fields, wherein the unstructured information is based on information included in images of the first set of medical documents and in a format that is insertable into a table;
classifying, by the computing device, structured information from a first data field in the second set of medical documents and a portion of the unstructured information in the first set of medical documents to a common data field in the common set of data fields, wherein the portion of unstructured information is included in an image of a medical document in the first set of medical documents;
inserting, by the computing device, the structured information and the unstructured information into the table based on the common set of data fields, wherein the common data field in the table includes the structured information from the first data field and the portion of unstructured information;
storing, by the computing device, the table based on the common set of data fields to allow for searching for information in both the first set of medical documents and the second set of medical documents using a query, wherein the query retrieves the structured information from the first data field and the portion of unstructured information from the common data field in the table;
receiving the query;
determining search results for the query using the set of common data fields associated with the schema, wherein the search results include information in the table from a subset of medical documents from the first set of medical documents and the second set of medical documents that are determined to match the query; and
displaying the search results in an interface, wherein the information from the subset of medical documents is displayed in a common data format.

2. The method of claim 1, further comprising:
tagging information in the first set of medical documents according to a first set of data fields;
tagging information in the second set of medical documents according to a second set of data fields; and
inserting the tagged information into the common set of data fields in the table.

3. The method of claim 2, wherein a second data field in the first set of data fields and the first data field in the second set of data fields correspond to the common data field in the set of common data fields.

4. The method of claim 1, wherein:
the common data format is a structured data format.

5. The method of claim 1, wherein:
the common data format is the image based format.

6. The method of claim 1, further comprising:
linking the second set of medical documents with the table; and
allowing a user to retrieve structured data for the second set of medical documents from the table.

7. The method of claim 1, wherein the plurality of medical documents is received from different medical providers.

8. The method of claim 1, wherein determining the unstructured information in the first set of medical documents relevant to the common set of data fields comprises:
determining a template for automatically determining a subset of the unstructured information from images from the first set of medical documents; and
automatically determining the subset of the unstructured information for images based on the template.

9. A non-transitory computer-readable storage medium containing instructions, that when executed, control a computer system to be configured for:
receiving a plurality of medical documents, the plurality of medical documents including a first set of medical documents in a first format in an image based format and a second set of medical documents in a second format in a structured data format;
determining a schema based on a review of an organizing principle to which a common set of data fields can be used to classify information from the first set of medical documents and the second set of medical documents;
determining, via extraction, unstructured information in the first set of medical documents relevant to the common set of data fields, wherein the unstructured information is based on information included in images of the first set of medical documents and in a format that is insertable into a table;

classifying structured information from a first data field in the second set of medical documents and a portion of the unstructured information in the first set of medical documents to a common data field in the common set of data fields, wherein the portion of unstructured information is included in an image of a medical document in the first set of medical documents;

inserting the structured information and the unstructured information into the table based on the common set of data fields, wherein the common data field in the table includes the structured information from the first data field and the portion of unstructured information;

storing the table based on the common set of data fields to allow for searching for information in both the first set of medical documents and the second set of medical documents using a query, wherein the query retrieves the structured information from the first data field and the portion of unstructured information from the common data field in the table;

receiving the query;

determining search results for the query using the set of common data fields associated with the schema, wherein the search results include information in the table from a subset of medical documents from the first set of medical documents and the second set of medical documents that are determined to match the query; and displaying the search results in an interface, wherein the information from the subset of medical documents is displayed in a common data format.

10. The non-transitory computer-readable storage medium of claim 9, further configured for:

tagging information in the first set of medical documents according to a first set of data fields;

tagging information in the second set of medical documents according to a second set of data fields; and compiling the tagged information into the common set of data fields.

11. The non-transitory computer-readable storage medium of claim 10, wherein a second data field in the first set of data fields and the first data field in the second set of data fields correspond to the common data field in the set of common data fields.

12. The non-transitory computer-readable storage medium of claim 9, wherein:

the common data format is a structured data format.

13. The non-transitory computer-readable storage medium of claim 9, wherein:

the common data format is the image based format.

14. The non-transitory computer-readable storage medium of claim 9, further configured for:

linking the second set of medical documents with the table; and allowing a user to retrieve structured data for the second set of medical documents from the table.

15. The non-transitory computer-readable storage medium of claim 9, wherein the plurality of medical documents is received from different medical providers.

16. An apparatus comprising:

one or more computer processors; and a non-transitory computer-readable storage medium comprising instructions, that when executed, control the one or more computer processors to be configured for:

receiving a plurality of medical documents, the plurality of medical documents including a first set of medical documents in a first format in an image based format and a second set of medical documents in a second format in a structured data format;

determining a schema based on a review of an organizing principle to which a common set of data fields can be used to classify information from the first set of medical documents and the second set of medical documents;

determining, via extraction, unstructured information in the first set of medical documents relevant to the common set of data fields, wherein the unstructured information is based on information included in images of the first set of medical documents and in a format that is insertable into a table;

classifying structured information from a first data field in the second set of medical documents and a portion of the unstructured information in the first set of medical documents to a common data field in the common set of data fields, wherein the portion of unstructured information is included in an image of a medical document in the first set of medical documents;

inserting the structured information and the unstructured information into the table based on the common set of data fields, wherein the common data field in the table includes the structured information from the first data field and the portion of unstructured information;

storing the table based on the common set of data fields to allow for searching for information in both the first set of medical documents and the second set of medical documents using a query, wherein the query retrieves the structured information from the first data field and the portion of unstructured information from the common data field in the table;

receiving the query;

determining search results for the query using the set of common data fields associated with the schema, wherein the search results include information in the table from a subset of medical documents from the first set of medical documents and the second set of medical documents that are determined to match the query; and displaying the search results in an interface, wherein the information from the subset of medical documents is displayed in a common data format.

* * * * *